United States Patent [19]

Cevasco

[11] Patent Number: 5,214,198
[45] Date of Patent: May 25, 1993

[54] PROCESS FOR THE MANUFACTURE OF HALOMALEIC AND HALOFUMARIC ESTERS

[75] Inventor: Albert A. Cevasco, Somerset, N.J.

[73] Assignee: American Cyanamid Company, Stamford, Conn.

[21] Appl. No.: 812,521

[22] Filed: Dec. 20, 1991

[51] Int. Cl.$^5$ ............................................ C07C 67/317
[52] U.S. Cl. .................................... 560/192; 562/595
[58] Field of Search ......................... 560/192; 562/595

[56] References Cited

U.S. PATENT DOCUMENTS

| 4,515,974 | 5/1985 | Zecher et al. | 560/192 X |
| 4,539,424 | 9/1985 | Jenck | 560/192 X |
| 4,908,385 | 3/1990 | Bar-Tana et al. | 560/192 X |

Primary Examiner—José G. Dees
Assistant Examiner—Vera C. Clarke
Attorney, Agent, or Firm—John W. Hogan, Jr.

[57] ABSTRACT

There is provided a method of manufacture of dialkyl monohalomaleate and dialkyl monohalofumarate and mixtures thereof via a dehydrohalogenation of the appropriate dialkyl dihalosuccinate precursor in the presence of an aqueous base and a phase transfer catalyst.

7 Claims, No Drawings

PROCESS FOR THE MANUFACTURE OF HALOMALEIC AND HALOFUMARIC ESTERS

BACKGROUND OF THE INVENTION

Monohalomaleic esters and monohalofumaric esters are useful in the preparation of pyridine-2,3-dicarboxylic esters which are key intermediates in the production of a class of highly potent herbicidal agents, 2-(imidazolin-2-yl)nicotinic acids, esters and salts. Monohalomaleic esters and monohalofumaric esters are also useful in the preparation of anilinofumarate which is an important intermediate in the manufacture of 2-(2-imidazolin-2-yl)quinoline-3-carboxylic acid herbicidal agents. Descriptions of the use of these important halomaleate and halofumarate compounds in the manufacture of imidazolinyl herbicidal agents may be found in co-pending application Ser. No. 538,861 filed on Jun. 15, 1990 and U.S. Pat. No. 4,904,816.

Representative of the methods used to prepare halomaleic or halofumaric esters from dihalosuccinic esters are those which entail high reaction temperatures, excess quantities of organic solvent and long reaction times such as described in Japan 76 16,406 and Japan 68 29,571.

It is an object of this invention to provide an improved method for the manufacture of monohalomaleic and monohalofumaric esters from dihalosuccinic esters which employs milder reaction conditions and shorter reaction times.

SUMMARY OF THE INVENTION

There is provided a process for the manufacture of a compound of formula I

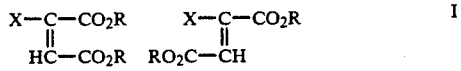

wherein X is halogen and R is $C_1$-$C_6$alkyl, which comprises reacting a compound of formula II

wherein X and R are as described for formula I, with at least one molar equivalent of a base in the presence of a phase transfer catalyst and water.

The process of the invention is an improved process with effectively lower reaction temperatures, significantly shorter reaction times and minimum organic solvent requirements.

DESCRIPTION OF THE INVENTION

The present invention relates to an improved process for the manufacture of monohalomaleate and monohalofumarate compounds via the appropriate dihalosuccinate precursor. Monohalomaleate and monohalofumarate compounds are important intermediates in the preparation of a new class of highly potent 2-(imidazolin-2-yl)nicotinate and -quinoline -3-carboxylate herbicidal agents.

It has now been found, that dialkyl monohalomaleates and monohalofumarates of formula I may be prepared efficiently and effectively from dialkyl dihalosuccinates of formula II by reacting the formula I compounds with at least one molar equivalent of an alkali metal base in the presence of a phase transfer catalyst (PTC) and water, optionally at an elevated temperature. The reaction is shown in flow Diagram I wherein X is halogen and R is $C_1$-$C_6$alkyl.

Flow Diagram I

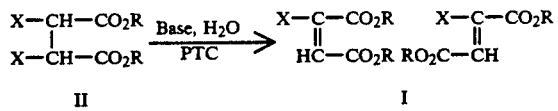

The term halogen, as used in the specification and claims, designates Cl, Br and I. Bases suitable for use in the inventive process are alkali metal hydroxides such as NaOH or KOH, alkali metal carbonates such as $Na_2CO_3$, $K_2CO_3$ and the like and alkali metal bicarbonates such as $NaHCO_3$, $KHCO_3$ and the like. Alkali metal carbonates such as $Na_2CO_3$ are preferred. Phase transfer catalysts suitable for use in the process of the invention include tetraalkylated ammonium salts such as tetra-n-butylammonium bromide, tricaprylmethylammonium hydrogen sulfate, benzyltriethylammonium chloride, tributylmethylammonium chloride and the like.

In accordance with the method of invention a dihalosuccinnic ester of formula II is reacted with about 1.0 to 1.5 molar equivalents of an alkali metal base, preferably an alkali metal carbonate, in the presence of a phase transfer catalyst, preferably a tetraalkylated ammonium salt, optionally at an elevated temperature of about 45°-75° C., preferably about 50°-60° C. to form the formula I monohalomaleic and monohalofumaric ester product.

Advantageously, the rate of formation of the formula I product is greatly enhanced by the presence of a phase transfer catalyst and is further increased by increased temperature. Therefore, effective reaction rates may be accomplished by increasing the reaction temperature to a range of about 45°-75° C.

The product may be isolated by separating the reaction mixture phases and optionally distilling the organic phase. Phase separation may be enhanced by the addition of a suitable organic solvent such as toluene, benzene, xylene, mono or dichlorobenzene, methylene chloride, carbon tetrachloride, methyl isobutylketone, and the like.

The process of the present invention is further illustrated by the following examples which are solely demonstrative thereof and not limited thereby.

Unless otherwise noted, all parts are parts by weight. The term HPLC designates high performance liquid chromatography and the term HRGC designates high resolution gas chromotography.

EXAMPLE 1

Preparation of diethyl chlorofumarate and diethyl chloromaleate from diethyl dichlorosuccinate A stirred mixture of anhydrous sodium carbonate (9.8 g, 0.093 mole) and tetra-n-butylammonium bromide (0.9 g, 0.0028 mole) in 35 g water is treated with diethyl dichlorosuccinate (15.0 g, 0.062 mole) and heated at 55° C. for 2 hours, until reaction is complete by HPLC analysis. The reaction mixture is cooled to room temperature and extracted with toluene. The extracts are combined and distilled to give the title product in 95% yield as a 6:1 mixture of diethyl chlorofumarate and diethyl chloromaleate, respectively, identified by HRGC analysis.

EXAMPLE 2

Kinetic study of the process of the invention.

Presence of a phase transfer catalyst

A stirred mixture of anhydrous sodium carbonate (16.0 g, 0.15 mole) and tetra-n-butylammonium bromide (2.2 g, 0.0068 mole) is treated with diethyl dichlorosuccinate (53.1 g, 0.22 mole). The reaction mixture is heated to 60° C. and held at that temperature until the reaction is complete. Periodically, samples are removed and analyzed by gas chromatography. The results are shown in Table I below.

When the reaction is complete, methylene chloride is added to the reaction mixture and the phases are separated. The organic phase is distilled to give the title product, 45.1 g, (97.4% pure) in 96.6% yield consisting of 83.3% diethyl chlorofumarate and 14.1% diethyl chloromaleate, identified by HRGC analysis.

TABLE I

Rate Of Formation Of Chlorofumarate And Chloromaleate In The Presence Of a Phase Transfer Catalyst

| Reaction Time (Minutes) | % DEDCS[1] | % DECF[2] | % DECM[3] |
|---|---|---|---|
| 0 | 91.6 | 0 | 0 |
| 30 | 8.2 | 75.9 | 9.5 |
| 50 | 5.5 | 81.2 | 11.2 |
| 90 | 0 | 83.7 | 13.8 |

[1]Diethyl dichlorosuccinate
[2]Diethyl chlorofumarate
[3]Diethyl chloromaleate

As can be seen in Table I, the reaction is essentially complete in about 1 hour at 60° C. and the overall yield is essentially quantitative.

EXAMPLE 3

Comparative kinetic study

Absence of a phase transfer catalyst

A stirred mixture of anhydrous sodium carbonate (5.3g, 0.05 mole) in water is treated with diethyl dichlorosuccinate (17.7g, 0.065 mole). The reaction mixture is heated to 60° C. and held at that temperature until the reaction is spent. Samples are removed periodically and analyzed as described in Example 2. The results are shown in Table II below. The measurement taken at reaction time equal to zero was taken after starting to heat to 60° C.

TABLE II

Rate Of Formation Of Chlorofumarate And Chloromaleate In The Absence Of A Phase Transfer Catalyst

| Reaction Time (Minutes) | % DEDCS[1] | % DECF[2] | % DECM[3] |
|---|---|---|---|
| 0 | 94.2 | 3.5 | 0 |
| 80 | 48.0 | 44.3 | 5.3 |
| 130 | 37.8 | 53.1 | 6.7 |
| 190 | 29.2 | 60.5 | 7.8 |
| 240 | 23.3 | 65.5 | 8.8 |
| 280 | 19.6 | 68.0 | 9.3 |
| 355 | 15.7 | 72.0 | 9.9 |

[1]Diethyl dichlorosuccinate
[2]Diethyl chlorofumarate
[3]Diethyl chloromaleate

As can be seen in Table II, the reaction is still incomplete after 6 hours at 60° C.

What is claimed is:

1. A process for the manufacture of a compound of formula I

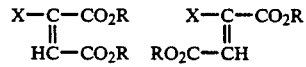

wherein X is halogen and R is $C_1$-$C_6$ which comprises reacting a compound of formula II

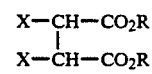

wherein X and R are as described for formula I, with at least one molar equivalent of a base at about 45°–75° C. in the presence of a tetraalkylated ammonium salt phase transfer catalyst and water.

2. The process according to claim 1 wherein the base is present in the amount of about 1.0 to 1.5 molar equivalents.

3. The process according to claim 1 wherein the base is an alkali metal hydroxide, carbonate or bicarbonate.

4. The process according to claim 3 wherein the base is an alkali metal carbonate.

5. The process according to claim 1 wherein the phase transfer catalyst is tetra-n-butylammonium bromide.

6. The process according to claim 1 wherein the temperature is about 50°–60° C.

7. The process according to claim 1 wherein X is Cl and R is methyl or ethyl.

* * * * *

UNITED STATES PATENT OFFICE
CERTIFICATE OF CORRECTION

Patent No. 5,214,198            Dated May 25, 1993

Inventor(s) Albert A. Cevasco

It is certified that error appears in the above-identified patent and that said Letters Patent is hereby corrected as shown below:

In Claim 1, Col. 4, line 28, "$C_1$-$C_6$ which" should be -- $C_1$-$C_6$ alkyl, which --.

Signed and Sealed this

First Day of February, 1994

BRUCE LEHMAN

Attest:

Attesting Officer            Commissioner of Patents and Trademarks